United States Patent [19]

Motonaga et al.

[11] Patent Number: 4,565,780

[45] Date of Patent: Jan. 21, 1986

[54] METHOD FOR DETERMINATION OF CHOLINESTERASE ACTIVITY

[75] Inventors: Hideo Motonaga; Masahiro Naito, both of Kanagawa, Japan

[73] Assignee: Shino-Test Laboratory Co., Ltd., Tokyo, Japan

[21] Appl. No.: 395,029

[22] PCT Filed: Dec. 23, 1981

[86] PCT No.: PCT/JP81/00405

§ 371 Date: Jun. 21, 1982

§ 102(e) Date: Jun. 21, 1982

[87] PCT Pub. No.: WO82/02212

PCT Pub. Date: Jul. 8, 1982

[30] Foreign Application Priority Data

Dec. 25, 1980 [JP] Japan ................................ 55-182910

[51] Int. Cl.$^4$ ........................... C12Q 1/46; C12Q 1/26
[52] U.S. Cl. ........................................ 435/20; 435/25; 435/810; 435/817
[58] Field of Search ................. 435/20, 25, 810, 817

[56] References Cited

U.S. PATENT DOCUMENTS 3,959,351  5/1976  Day et al. ............................ 424/308
4,271,310  6/1981  Watanabe et al. ................... 424/309

FOREIGN PATENT DOCUMENTS 0060059  9/1982  European Pat. Off. .............. 435/20

OTHER PUBLICATIONS

Yano et al., Agr. Biol. Chem., 33 (5), 689–697, (1969).

Primary Examiner—Esther M. Kepplinger
Attorney, Agent, or Firm—Gordon W. Hueschen

[57]     ABSTRACT

In the method according to the present invention and with the use of reagents according to the present invention, it has been possible to perform routine examinations of activities of cholinesterase in serum, that is of high importance for examinations of liver function disease. A kinetic determination method with using an autoanalyzer can be performed in reacting a test sample of serum with p-hydroxybenzoyl choline as a substrate in presence of p-hydroxybenzoic acid hydroxylase.

11 Claims, 3 Drawing Figures

METHOD FOR DETERMINATION OF CHOLINESTERASE ACTIVITY

FIELD OF THE INVENTION

This invention relates to a method for determination of activity of cholinesterase (hereafter called Ch—E) in serum and reagents to perform this method.

BACKGROUND OF THE INVENTION

Cholinesterase is a generic term for those enzymes that hydrolyze choline ester to choline and an organic acid.

In the body exist true cholinesterase and pseudocholinesterase. True Ch—E exists in red blood-corpuscle, in the nervous-system, as well as in muscles and has an effect to decompose specifically acetyl choline or acetyl-$\beta$-methylcholine. On the other hand, pseudo Ch—E exists in serum, in liver and pancreas, and it decomposes specifically benzoyl-choline and mainly the cholinester of fatty acids with a longer chain of carbon atoms, such as for example butyrylcholine. Of these two kinds of Ch—E, the quantitative determination of the activity of pseudo Ch—E especially in serum is of highest importance, for the examination of liver disease, because the activity of pseudo Ch—E decreases greatly at times of disease of the liver, especially in cases of chronic damages of liver parenchyma and liver cirrhosis. In addition, such a determination is of importance for the treatment of poisonings with phosphorous containing compounds used in agriculture and furthermore for examination at therapeutic treatment by means of an anticholinesterase preparation.

For determination of Ch—E activity, gas-analysis, $\Delta$ pH-method, colorimetric analysis, UV-procedure, fluorescent procedure and electrode-method are known. In cases of clinical routine examinations, $\Delta$ pH-method and colorimetric analysis are most conventional. In case of $\Delta$ pH-method in which acetic acid formed by Ch—E effect is determined by means of a pH-indicator, a complicated correction of the strongly deviated calibration-curve is necessary and the accuracy is uncertain.

Among colorimetric analysis, there are the DTNB-procedure (Garrv. D. J., Clin. Chem.11.(2):91 (1965)) and the enzyme procedure (Kunihide Gomi: Rinshobyori Special nunber 29: 145(1977)).

In case of DTNB procedure, acetyl thiocholine, butyryl-thiocholine are used as substrate and the thus formed thiocholine is mixed with 5.5'-dithio-bis-2-nitrobenzoic acid (DTNB) and the density of yellow colour in comparison with glutathione in reduced form as standard of a SH-compound is measured spectrometrically. The exactness of the determination is therefore interfered by bilirubin and a reducing substance and furthermore the stability of the reagents during storage is not satisfctry.

In case of enzyme-procedure, benzoyl choline and ortho-toluoyl-choline are used as substrate and the choline formed by enzyme reaction is changed to betaine with choline oxidase. By the action of $H_2O_2$ thus formed, an oxidizing condensation of 4-aminoantipirin with phenol in presence of peroxidase occurs with colouring that has to be measured spectrometically. The determination is therefore influenced by additional choline that is formed through decomposition of phospholipid in serum, because choline shall be converted with choline oxidase. Besides, such determination is interfered by reducing substances such as bilirubin and ascorbic acid. Furthermore, this process is not usuful for determination by means of an auto-analyser.

To overcome the disadvantages of known processes, a method to assay Ch—E activity in serum was suggested by the applicant of this invention according to Japanese patent application No. 093896/1980. In this method p-hydroxybenzoic-acid that is formed from p-hydroxybenzoyl-choline as a substrate through enzymatic effect of Ch—E and has been oxidatingly condensed with 4-aminoantipyrin in presence of an oxidizing agent to obtaining a coloured compound and the degree of colouring is being measured.

DISCLOSURE OF THE INVENTION

The object of the invention is an advanced development of the method according to Japanese patent application No. 93896/1980 and a method for enzymatic determination of cholinesterase characterized in that p-hydroxy-benzoic acid (p-HBA) that is formed from a p-hydroxy-benzoyl-choline (p-HBC) as substrate through the effect of Ch—E is reacted with p-hydroxybenzoat-hydroxylase (p-HBH) under oxidizing condition in the presence of coenzyme, nicotinamide adeninedinucleotide phosphate in reduced form (NADPH), whereby the difference of the degree of the extinction value by NADPH-conversion to nicotinamide-adenine-dinucleotide-phosphate in oxidized form (NADP+) or the degree of the oxygen-consumption in the reaction phase is measured and reagents to perform the method.

p-Hydroxybenzoyl-choline-derivatives (p-HBC), which should be used according to the invention, have the general formula:

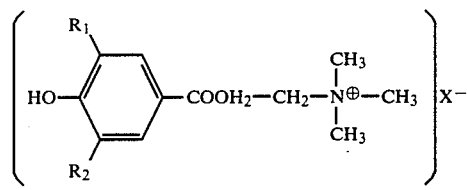

whereby $R_1$ and $R_2$ mean a hydrogen atom, or one of the $R_1$ and $R_2$ is a lower alkoxygroup with $C_1$ to $C_4$, and X means a halogen atom.

The reactions by the determination according to the invention can be shown in following chemical scheme:

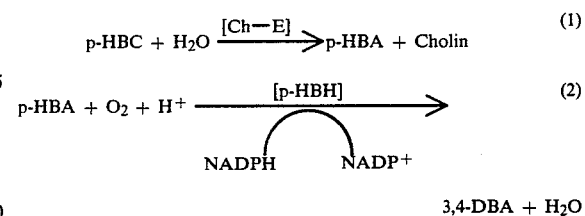

3,4-DBA + $H_2O$ p-Hydroxybenzoic acid (p-HBA) that is formed according to the reaction (1) will be converted to 3,4-dihydroxy benzoic acid (3,4-DBA) in the presence of coenzyme, NADPH, according to the reaction (2) by the enzymatic effect of p-hydroxy-benzoate-hydroxylase, whereby extinction value sinks under oxidizing reaction of NADPH to NADP+.

Ch—E activity is determined by measuring the decrease in extinction value at 340 nm, in which measurement the rate of decrease is to be measured or the decrease after a certain period of time is measured. In the latter case, the decrease is measured without stopping the reaction or by stopping with the below mentioned inhibitors.

The following substances can be used as reaction inhibitor: Neostigumin, eserine and organic phosphoric compounds with inhibitional activities that are known as inhibitors for Ch—E activity.

The activity of Ch—E can further be measured by determination of consumption-speed of oxygen dissolved in reaction phase by effect of p-Hydroxy-benzoate-hydroxylase by mean of oxygen-electrodes.

Furthermore, the decrease of fluorescence in NADPH can be measured by means of a photoelectrical fluorophotometer.

The method according to the invention is neither interfered with by reducing substances such as bilirubin and ascorbic acid in the serum, nor by choline from phospholipid. Determination of the Ch—E activity can be executed easily and speedily by means of a kinetic determination method, while using a chemical autoanalyser that can treat a number of samples.

p-Hydroxy-benzoate hydroxylase to be used according to the invention is prepared from bacteria belonging to pseudomonas, for example *Ps. dacunhae, Ps. desmolytica, Ps. fluorescens, Ps. putida*, (Keiji Yano, Kei Arima, Agr. Biol.-chem., 33 (5): 689 (1969)).

p-Hydroxybenzoyl-choline as a substrate to be used according to the invention shows a high solubility and has a storage life of more than 2 weeks if kept in cool and dark places, even if kept in a water solution. The preparation of p-hydroxybenzoyl-choline is performed according to the usual and known methods. It can be prepared in the following way, for example: p-Acetoxybenzoic acid chloride is mixed with N,N-dimethylethanolamine in an organic solvent, then after cooling, mixed with methyl halide and the reaction mixture dissolved in a mixture of N,N dimethyl formamide and hydrazine hydrate.

The optimal pH-value at enzymatic reaction of Ch—E as the substrate used according to the invention is between 7.5 and 9.5, preferably about at 8.2. As a buffer for maintaining pH-value of the reaction-solution following substances might be used:

Trishydroxymethyl-amino-methane, glycylglycine, phosphates, borates, pyrophosphoric acid, barbital, N,N-Bis-(2-hydroxyethyl)glycine, N-tris-(hydroxymethyl)-methyl-glycine.

An addition of the corresponding quantity of flavin-adenine-dinucleotides (abbreviated FAD) is of advantage for enzymatic determination according to the process of the invention, because p-hydroxy-benzoate-hydroxylase represents the enzymes connected with FAD.

According to the difference of the enzyme to be used, which can be prepared form the culture solution of the above mentioned bacteria, an addition of salicyclic acid in a quantity of about 5 to 15 mM results in a linear relation at the enzymatic reaction.

Because the reagents and enzymes according to invention can be used in an extensive range of concentration without impairing the results for determination of Ch—E activity, a strict limitation of the quantity is not necessary. However, the preferable quantities are given as follows:

For enzymes 200 to 5000 U/l, preferably 220 to 700 U/l
For coenzymes 0.1 to 0.7 mM, preferably 0.3 to 0.5 mM
For substrate 0.2 to 20 mM, preferably 0.5 to 2 mM
For FAD 0.1 to 30 μM, preferably 1.0 to 5 μM

The following Examples explain the invention further without limiting the scope of the invention of this application.

EXAMPLE 1

(1) Reagents

1. Composition (concentration of solution ready for use):

Trishydroxy-methyl-amino-methane-maleic acid-buffer solution: 50.0 mM
p-hydroxybenzoyl-choline-iodide: 1.0 mM
FAD-2 Na: 0.003 mM
NADPH-4 Na: 0.3 mM
p-hydroxy-benzoate-hydroxylase: 700 U/l 2. Preparation:

6.06 g trishydroxy-methyl-aminomethane are dissolved in about 800 ml water and are adjusted with the aqueous solution of maleic acid to pH 8.2. Then 351 mg p-hydroxy benzoyl choline iodide, 2.5 mg FAD-2 Na, 272 mg NADPH-4 Na, and 700 U p-hydroxybenzoate-hydroxylase are added. With the solution thus prepared, the water will be filled up to 1,000 ml to produce the measuring solution.

(2) Operation for Determination 3 ml of the measuring solution are preheated to 37° C. (it takes about 3 minutes) and mixed with 50 μl serum. Decrease of the extinction is to be read immediately at 340 nm continuously with the employment of the autoanalyzer Hitachi 705 TM.

Figure 1:
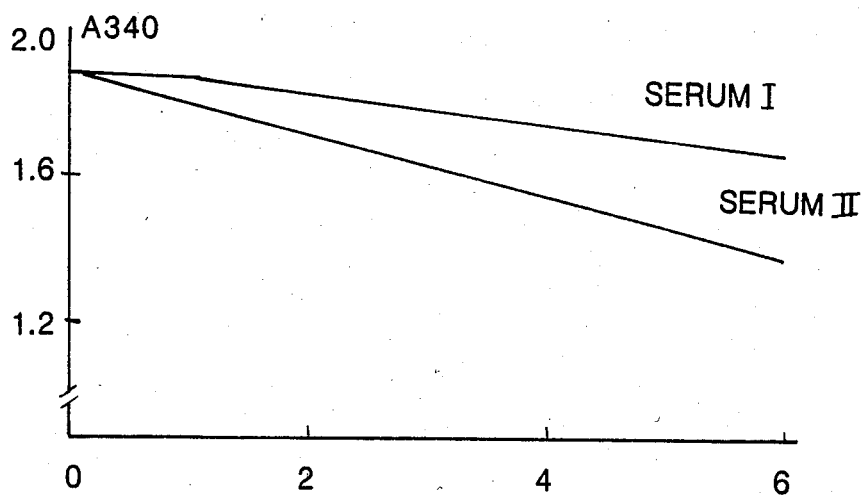
FIG. 1 of the attached drawing shows the mutual dependence between period of reaction at incubation at usage of 50 ||1 serum and NADPH according to the method of the invention.

As shown in FIG. 1, the results of examination with the two types of serum show that the extinction decreases during the course of the reaction. After speed of reaction becomes constant, the activity of Ch—E can be calculated according to the following formula:

$$1 \text{ U/l} = \frac{\Delta A340 \times (\text{quantity of solution}) \times 1,000}{(\text{molecular coefficient of extinction}) \times (\text{quantity of serum})}$$

In this formula, A340 has the meaning of extinction-difference in a period of 1 minute at 340 nm.

The molecular coefficient of extinction of NADPH is 6.22.

Hereafter in the Table 1, the examination-results of an activity-determination according to working process as mentioned above are shown, while using respectively 50 ml test sample of serum that was diluted ¼ to 4/4 with water.

TABLE 1

| dilution of serum | 1/4 | 2/4 | 3/4 | 4/4 |
|---|---|---|---|---|
| activity of Ch—E (U/l) | 142 | 294 | 412 | 569 |

Figure 2:
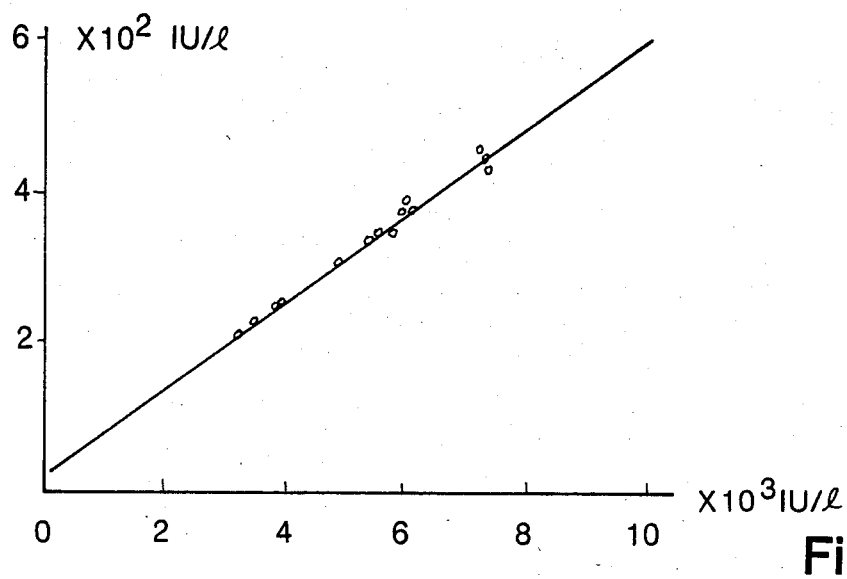
FIG. 2 shows the mutual dependence between the method according to the invention and the already known butyryl-thiocholine procedure.

In FIG. 2, the examination-results of activity of Ch—E of 15 test samples of serum in comparing with the butyryl-thiocholine DTNB-method (G. Szasz: Clin. Chem. Acta., 19:191:1968) are shown.

EXAMPLE 2

The experiment of Example 1 was repeated, wherein pH-value of trishydroxymethylaminomethanemaleic acid buffer solution was changed to 8.5 and 25 mg FAD-2 Na and 220 U p-hydroxy benzoate-hydroxylase were used.

The results were comparatively as good as those in example 1.

EXAMPLE 3

(1) Reagents

1. Composition (concentration of solution ready for use):

hydroxy-methyl-amino-methane maleic-acid buffer solution: 50.0 mM
p-hydroxy benzoic-choline-iodide: 1.0 mM
FAD-2 Na: 0.003 mM
NADPH-4 Na: 1.5 mM
p-hydroxy benzoic-acid-hydroxylase: 700 U/l 2. Preparation:

6.06 g trishydroxy-methyl-amino-methane are dissolved in about 800 ml water and are adjusted with the aqueous solution of maleic-acid to pH8.2. Then 351 mg p-hydroxy-benzoyl choline-iodide, 2.5 mg FAD-2 Na, 1.35 g NADPH-4 Na, and 700 U p-hydroxy-benzoic-acid hydroxylase are added. With the solution thus prepared, the water will be filled up to 1,000 ml to prepare measuring solution.

(2) Operation for Determination

Measuring solution is preheated to 37° C. and introduced to a chamber that contains oxygen detector and 20 μl serum are added. The decrease of oxygen concentration of the solution is measured with the oxygen detector (Stadt. Glucoseanalysator S-80 TM: Maker: AIC-Werke).

Figure 3:
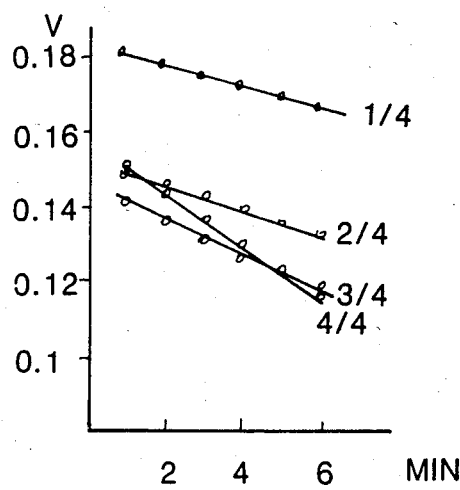
FIG. 3 shows the decrease of oxygen concentration of the solution using a diluted serum as sample according to Example 2.

As shown in FIG. 3 of Drawing, the oxygen concentration (Volt.) decreases during the course of reaction. Hereafter the examination results of activity determination according to working process as mentioned in Example 1 are shown, using respectively test sample of serum that was diluted to 1/4 to 4/4 with water. The results were completely satisfactory.

(3) Calculation of activity-units of Ch—E

1. Above described working process for determination is to be execute with 20 μl serum of a preknown unit. The activity of the sample is shown in relation to measured value.

$$\text{Test sample of serum (U/l)} \quad a \times \frac{c}{b}$$

$a$ = Standard serum (U/l)
$b$ = Measure value of standard serum (mV/min)
$c$ = Measure value of test sample of serum (mV/min)

2. Activity of the test sample of serum can furthermore be calculated according to reduction of oxygen concentration of the solution during reaction from 20 μl p-hydroxybenzoic-acid with a known concentration.

$$\text{Test sample of serum (U/l)} = \frac{d \times c \times 10^3}{b}$$

$$(c/b \times 0.02a \times 5 \times 10^4)$$

$a$ = p-hydroxy-benzoic acid (mM)
$b$ = decrease of oxygen concentration in course of reaction (mV/min)
$c$ = measure value of test sample of serum (mV/min)

TABLE 2

| dilution of serum | 1/4 | 2/4 | 3/4 | 4/4 |
|---|---|---|---|---|
| activity of Ch—E (U/l) | 3.0 | 3.9 | 5.0 | 7.0 |

EXAMPLE 4

The experiment of example 3 was repeated, wherein pH-value was changed to 8.5 and 25 mg FAD-2 Na and 220 U of p-hydroxybenzoic acid hydroxylase were used. The results of the examination were comparatively as good as those in example 3.

EXAMPLE 5

(1) Reagents

1. Composition (concentration of solutions ready for use):

(i)

Trishydroxymethylaminomethane maleic acid buffer solution: 50 mM
FAD-2 Na: 0.003 mM
p-hydroxy benzoic hydroxylase: 1,000 U/l
NADPH-4 Na: 0.45 mM (ii)

Trishydroxymethylaminomethane maleic acid buffer solution: 50 mM
p-hydroxy benzoyl choline iodide: 1.5 mM (iii)

Aqueous solution of neostigmin: 20 mM

2. Preparation:

(i)

6.06 g trishydroxy-methyl-amino-methane are dissolved in about 800 ml water and the pH value is adjusted with the aqueous solution of maleic acid to 8.2. Then 2.5 mg FAD-2 Na, 272 mg NADPH-4 Na, and 1,000 U p-hydroxy-benzoic-acid hydroxylase are added. With the solution thus prepared, the water will be filled up to 1,000 ml to prepare measuring solution.

(ii)

6.06 g trishydroxy-methyl-amino-methane are dissolved in about 800 ml water and are adjusted with the maleic-acid solution in water to pH8.2. Then 526.5 mg of p-hydroxy-benzoyl-choline-iodide are added. With the solution thus prepared, the water will be filled up to 1,000 ml.

(iii)

6 g neostigmin are dissolved in about 1,000 ml of water.

2. Operation for Determination:

(i)

blank value of reagent: 1.0 ml of reagents (i) is added to 20 μl water and, after a period of 5 minutes, the reagents (ii) are added to the obtained mixture at a temperature of 37° C. After an incubation period of 10 minutes at 37° C., 0.1 ml reagent (iii) are added and the reaction is immediately brought to a standstill. Then the extinction ($A_B$) is to be measured at 340 mm.

(ii) Test Sample 1.0 ml reagent (i) is added respectively to 20 μl test sample of serum and 20 μl standard serum and the obtained mixtures are added after 5 minutes at 37° C. to 0.5 ml reagent (ii).

After an incubation period of 10 minutes at 37° C., 0.1 ml of the reagent (iii) are added, and the reaction is immediately brought to a standstill. The extinctions of test sample of serum ($A_I$) and of standard serum ($A_s$) are to be measured at 340 nm.

(3) Calculation of Ch—E activity

Activity of Ch—E of serum can be calculated according to the following formula:

$$\frac{A_B - A_I}{A_B - A_S} \times \text{unit of standard serum}$$

Hereafter in Table 3, the examination results of an activity determination according to above mentioned working process are shown, while using respectively 50 μl of test sample of serum that was diluted ¼ to 4/4 with water.

TABLE 3

| dilution of serum | ¼ | 2/4 | ¾ | 4/4 |
|---|---|---|---|---|
| activity of Ch—E (U/l) | 155 | 314 | 461 | 617 |

EXAMPLE 6

The same examination of extinction according to example 5 was repeated, wherein pH value was changed to 8.5 and 0.03 mM FAD-2 Na and 330 U p-hydroxy benzoic acid hydroxylase were used. The results were as good as in example 5.

We claim:

1. The method for determination of cholinesterase activity by measuring the extinction decrease or the oxygen consumption, comprising the following steps:
(a) Subjecting a substrate having the formula:

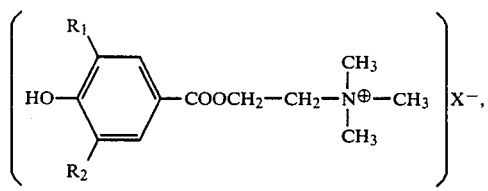

wherein $R_1$ and $R_2$ represent a hydrogen atom or one or both of $R_1$ and $R_2$ represent a lower-alkoxy group with 1 through 4 carbon atoms, and X represents a halogen atom, to hydrolysis by the action of cholinesterase to produce a p-hydroxybenzoic acid,
(b) reacting the p-hydroxybenzoic acid thus-produced with p-hydroxybenzoic acid hydroxylase in the presence of the coenzyme nicotinamide adenine dinucleotide phosphate in reduced form (NADPH), whereby the NADPH is oxidized to nicotinamide adenine dinucleotide phosphate (NADP), and
(c) measuring the extent of extinction decrease or oxygen consumption in the reaction mixture produced by conversion of the nicotinamide-adenine-dinucleotide phosphate in reduced form (NADPH) to the oxidized form (NADP).

2. Method according to claim 1 characterized in that the extinction is measured at 340 nm.

3. Method according to claim 1 characterized in that the speed of oxygen consumption in the reaction solution is measured by means of an oxygen electrode.

4. Method according to claim 1 characterized in that the reaction of p-hydroxy-benzoic-acid-hydroxylase is performed in the presence of flavin adenine dinucleotide (FAD).

5. Method according to claim 1 characterized in that the reaction of cholinesterase with substrate is performed at a pH value of 7.5 to 9.5.

6. Method according to claim 5 characterized in that the reaction is performed in the presence of a buffer.

7. Method according to claim 6 wherein the pH is about 8.2.

8. Reagent for determination of cholinesterase activity consisting essentially of a halide salt of p-hydroxybenzoylcholine optionally having one or two lower-(1-4 C atom)alkoxy groups on the phenyl ring in position adjacent to the p-hydroxy group, p-hydroxybenzoic acid hydroxylase, and coenzyme nicotinamide-adenine-dinucleotide-phosphate in reduced form (NADPH), and one or more additional ingredients selected from the group consisting of FAD, salicyclic acid, and buffer, the proportions of p-hydroxybenzoylcholine, p-hydroxybenzoic acid hydroxylase, and NADPH being such that, upon subjection of the reagent to cholinesterase, the p-hydroxybenzoylcholine converts to a benzoic acid, which reacts with the p-hydroxybenzoic acid hydroxylase to give a measurable oxidation of the NADPH to NADP.

9. Reagent according to claim 8 characterized in that it contains 0.02 to 20 mM p-hydroxybenzoyl choline, 0.1 to 0.7 mM nicotinamide-adenine-dinucleotide phosphate in reduced form, 200 to 5,000 U/l p-hydroxybenzoic acid hydroxylase, and 0.1 to 30 μM FAD buffered to pH 7.5 to 9.5.

10. Reagent according to claim 9 characterized in that buffer is tris-(hydroxymethyl)-aminomethane-maleic acid.

11. A method for determining the activity of cholinesterase

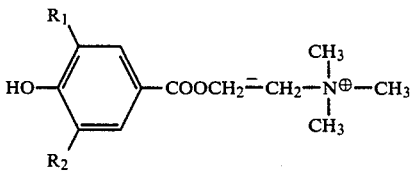

wherein $R_1$ and $R_2$ represent a hydrogen atom or one or both of $R_1$ and $R_2$ represent a lower alkoxy group with 1 to 4 carbon atoms
under conditions effective to transform said substrate into p-hydroxybenzoic acid and to oxidize said NADPH to NADP+ and measuring the decrease in extinction produced by the conversion of NADPH to NADP+.

* * * * *

UNITED STATES PATENT AND TRADEMARK OFFICE
CERTIFICATE OF CORRECTION

PATENT NO. : 4,565,780                          Page 1 of 2
DATED      : January 21, 1986
INVENTOR(S): Hideo Motonaga and Masahiro Naito It is certified that error appears in the above-identified patent and that said Letters Patent is hereby corrected as shown below:

Col. 1, line 46; "nunber" should read -- number --
Col. 1, line 50; "density" should read -- intensity --
Col. 1, line 56; "satisfactry" should read -- satisfactory --
Col. 2, line 1; "usuful" should read -- useful --
Col. 2, line 46; "alkoxygroup" should read -- alkoxy group --
Col. 2, line 49; insert -- the -- after "in"
Col. 2, approximately line 58, the lower half of the chemical scheme, on the curved line to the right just above "NADP+" there should be an arrow.
Col. 3, line 15; "mean" should read -- means --
Col. 3, line 59; "form" should read -- from --
Col. 3, line 60; "salicyclic" should read -- salicylic --
Col. 3, line 63; insert -- the -- after "to"
Col. 4, line 9; "|| 1" should read -- µ 1 --
Col. 7, line 3; "reagents" should read -- reagent --
Col. 8, line 45; "FAD" should read -- FAD, --
Col. 8, line 48; insert -- the -- after "that"
Col. 8, lines 50&51; insert after "cholinesterase" the rest of the sentence, -- comprising the steps of:
    mixing a liquid containing cholinesterase with a p-hydroxybenzoate hydroxylase, reduced nicotinamide adenine dinucleotide phosphate (NADPH) and a cation of the substrate --

UNITED STATES PATENT AND TRADEMARK OFFICE
CERTIFICATE OF CORRECTION

PATENT NO. : 4,565,780

DATED : January 21, 1986

INVENTOR(S) : Hideo Montonaga and Masahiro Naito

It is certified that error appears in the above-identified patent and that said Letters Patent is hereby corrected as shown below:

Col, 8, approximately line 55, in the formula, between "$COOCH_2$" and "$CH_2$" delete the little line above the bond.

Signed and Sealed this

Twentieth Day of May 1986

[SEAL]

Attest:

DONALD J. QUIGG

Attesting Officer

Commissioner of Patents and Trademarks